(12) United States Patent
Roszell et al.

(10) Patent No.: US 8,735,422 B2
(45) Date of Patent: May 27, 2014

(54) CATIONIC PHARMACEUTICALLY ACTIVE INGREDIENT CONTAINING COMPOSITION, AND METHODS FOR MANUFACTURING AND USING

(75) Inventors: James A. Roszell, Las Vegas, NV (US); Jie Zhang, Henderson, NV (US)

(73) Assignee: Skinvisible Pharmaceuticals, Inc., Las Vegas, NV (US)

( * ) Notice: Subject to any disclaimer, the term of this patent is extended or adjusted under 35 U.S.C. 154(b) by 64 days.

(21) Appl. No.: 12/701,367

(22) Filed: Feb. 5, 2010

(65) Prior Publication Data

US 2010/0204262 A1 Aug. 12, 2010

Related U.S. Application Data

(60) Provisional application No. 61/150,673, filed on Feb. 6, 2009.

(51) Int. Cl.
*A61K 31/44* (2006.01)
(52) U.S. Cl.
USPC .......................................................... 514/293
(58) Field of Classification Search
USPC .......................................................... 514/293
See application file for complete search history.

(56) References Cited

U.S. PATENT DOCUMENTS

| | | | |
|---|---|---|---|
| 4,059,463 A * | 11/1977 | Aonuma et al. | 75/349 |
| 4,971,800 A | 11/1990 | Chess et al. | |
| 5,002,769 A | 3/1991 | Friedman | |
| 5,045,317 A | 9/1991 | Chess et al. | |
| 5,051,260 A | 9/1991 | Chess et al. | |
| 5,051,489 A * | 9/1991 | O'Lenick, Jr. | 528/26 |
| 5,508,024 A | 4/1996 | Tranner | |
| 5,705,532 A | 1/1998 | Modak et al. | |
| 6,436,376 B1 | 8/2002 | Hansenne et al. | |
| 6,582,683 B2 | 6/2003 | Jezior | |
| 6,756,059 B2 | 6/2004 | Roszell et al. | |
| 6,846,846 B2 | 1/2005 | Modak et al. | |
| 6,936,735 B2 * | 8/2005 | Chaudhuri | 564/156 |
| 7,452,416 B2 * | 11/2008 | Evers | 106/447 |
| 2003/0044374 A1 | 3/2003 | Roszell et al. | |
| 2005/0191247 A1 | 9/2005 | Drake et al. | |
| 2007/0160559 A1 | 7/2007 | Roszell | |
| 2007/0212320 A1 | 9/2007 | Demitz et al. | |
| 2008/0193489 A1 | 8/2008 | De Armond et al. | |

FOREIGN PATENT DOCUMENTS

| | | |
|---|---|---|
| EP | 0 231 080 B1 | 4/1989 |
| EP | 1 997 472 A1 | 12/2008 |
| WO | WO 2007/070643 * | 6/2007 |

OTHER PUBLICATIONS

International Search Report and Written Opinion dated Apr. 2, 2010 for PCT/US 10/23352.
"Biguanides," http://www.uaf.edu/iacuc/training/module_3/3_biguanide.html, 1 page (Jun. 22, 2001).
"Chlorhexidine Digluconate," 2 pages (Sep. 30, 1996).
"Chlorhexidine digluconate—Identification, toxicity, use, water pollution potential, ecological toxicity and regulatory information," http://www.pesticideinfo.org/Detail_Chemical.jsp?Rec$_{13}$ Id=PC36769, 6 pages (Date Printed Dec. 12, 2005).
"Chlorhexidine Gluconate," http://www.en.wikipedia.org/wiki/Chlorhexidine_Gluconate, 1 page (Nov. 17, 2005).
"Did you know? Quick facts about hand scrubbing," 1 page (Jul. 2001).
"Hibiclens Material Safety Data Sheets," http://www.regentmedical.com/americas/hibiclens_data_sheets.html, 5 pages (Date Printed Dec. 12, 2005).

* cited by examiner

*Primary Examiner* — Shirley V Gembeh
(74) *Attorney, Agent, or Firm* — Merchant & Gould, P.C.

(57) ABSTRACT

A cationic pharmaceutically active ingredient containing composition is provided. The composition includes a cationic pharmaceutically active ingredient, a hydrophobic polymer/hydrophilic polymer adduct comprising a poly(vinylpyrrolidone/alkylene) polymer and a polymer comprising carboxylic acid groups, hydroxyl groups, or a mixture of carboxylic acid groups and hydroxyl groups, a compatibilizing amount of a long chain organic acid having a carbon chain of at least 8 carbon atoms, and at least about 50 wt. % water.

19 Claims, 5 Drawing Sheets

CATIONIC PHARMACEUTICALLY ACTIVE INGREDIENT CONTAINING COMPOSITION, AND METHODS FOR MANUFACTURING AND USING

This application claim priority, to the extent appropriate, to U.S. Application Ser. No. 61/150,673 that was filed with the United States Patent and Trademark Office on Feb. 6, 2009. The entire disclosure of U.S. Application Ser. No. 61/150,673 is incorporated herein by reference.

FIELD OF THE INVENTION

The invention relates to a cationic pharmaceutically active ingredient containing composition, to a method for using a cationic pharmaceutically active ingredient containing composition, and to a method for manufacturing a cationic pharmaceutically active ingredient containing composition.

BACKGROUND

Skin bonding polymer compositions are described that include a hydrophobic polymer/hydrophilic polymer adduct and other components. These compositions can be provided as topical compositions to be applied to skin tissue. Exemplary skin bonding polymer compositions are described in U.S. Pat. No. 6,756,059, assigned to Skinvisible Pharmaceuticals, Inc. In addition, see U.S. Patent Publication No. 2002/0051797. Because of the highly hydrophobic nature of certain hydrophobic polymer/hydrophilic polymer adducts described in U.S. Pat. No. 6,756,059, ionic and water-soluble active ingredients may have difficulty being absorbed into or contained within the hydrophobic polymer/hydrophilic polymer adduct. Because a large number of active ingredients are salts, it is desirable to provide a composition that absorbs or binds ionic and water-soluble active ingredients and allows the active ingredients to be released, over time, to skin tissue. Furthermore, although certain hydrophobic polymer/hydrophilic polymer adducts can be highly hydrated, the hydrophilic compartment within certain hydrophobic polymer/hydrophilic polymer adducts may be relatively small thereby limiting the availability of the compartment to relatively small molecules such as molecules having a molecular weight of less than about 100.

In a topical delivery composition, it is often difficult to control the delivery rate of a cationic pharmaceutically active ingredient such as a cationic drug. An exemplary cationic pharmaceutically active ingredient is Imiquimod. Imiquimod is generally recognized as an immune response modifier, is considered a weak base, and is the active ingredient in Aldara® cream sold in the United States by Graceway Pharmaceuticals, LLC. Aldara® cream is often used for treatment of actinic keratosis, basal cell carcinoma, and external genital warts. Imiquimod is a potent drug with a high level of irritation. When applying a topical delivery composition containing Imiquimod, it is desirable for the composition to release Imiquimod at a rate sufficient to provide desired activity. The rate of release, however, should not be so great as to cause an undesirable side effect. For these reasons, it is desirable to control the delivery of Imiquimod. Furthermore, because Imiquimod tends to cause a high level of irritation, it is desirable to be able to use less Imiquimod while obtaining a desired level of performance.

SUMMARY

A cationic pharmaceutically active ingredient containing composition is provided. The cationic pharmaceutically active ingredient containing composition includes: about 0.0001 wt. % to about 5 wt. % cationic pharmaceutically active ingredient; at least about 3 wt. % of a hydrophobic polymer/hydrophilic polymer adduct comprising a polyvinylpyrrolidone-alkylene) polymer and a polymer comprising carboxylic acid groups, hydroxyl groups, or mixture of carboxylic acid groups and hydroxyl groups; a compatibilizing amount of a long chain organic acid having a carbon chain of at least about 8 carbon atoms; and at least about 50 wt. % water.

A method of using a cationic pharmaceutically active ingredient containing composition is provided. The method includes a step of applying a cationic pharmaceutically active ingredient containing composition to skin tissue. The cationic pharmaceutically active ingredient containing composition includes: about 0.0001 wt. % to about 5 wt. % cationic pharmaceutically active ingredient; at least about 3 wt. % of a hydrophobic polymer/hydrophilic polymer adduct comprising a poly(vinylpyrrolidone-alkylene) polymer and a polymer comprising carboxylic acid groups, hydroxyl groups, or mixture of carboxylic acid groups and hydroxyl groups; a compatibilizing amount of a long chain organic acid having a carbon chain of at least about 8 carbon atoms; and at least about 50 wt. % water. The step of applying the composition to skin tissue can include applying the composition as a cream or lotion to skin tissue and rubbing the composition onto the skin tissue.

A method for manufacturing a cationic pharmaceutically active ingredient containing composition is provided. The method includes steps of: forming a polymer adduct comprising a poly(vinylpyrrolidone-alkylene) polymer and a polymer comprising carboxylic acid groups, hydroxyl groups, or a mixture of carboxylic acid groups and hydroxyl groups in the presence of less than 1 wt. % water, if water is present at all; forming an emulsion containing the polymer adduct and water, wherein the water is present in an amount of at least about 50 wt. %; and adding a long chain organic acid having a carbon chain of at least about 8 carbon atoms and a cationic pharmaceutically active ingredient.

DETAILED DESCRIPTION

The topical composition includes the cationic pharmaceutically active ingredient, a polymer component for bonding to skin tissue and holding the cationic pharmaceutically active ingredient in place, a long chain organic acid to assist with holding the cationic pharmaceutically active ingredient to the polymer component, and water. Additional components that can be provided in the topical composition include release agents, pH adjusting agents, thickeners, emollients, moistures, preservatives, antioxidants, chelating agents, fragrances, and various carriers, diluents, and excipients.

The cationic pharmaceutically active ingredient composition provides a topical composition that can be applied to skin tissue and allow for the release of the cationic pharmaceutically active ingredient therefrom. In general, skin tissue refers to the external limiting tissue layer of an animal. In addition, the phrase "cationic pharmaceutically active ingredient" refers to those components that provide a pharmacological effect when applied to skin tissue. The cationic pharmaceutically active ingredients can be referred as cationic drugs or cationic active ingredients or cationic actives. Exemplary cationic drugs that can be contained within the topical composition for application to skin tissue include Imiquimod, Tetracycline, Streptomycin, Niacinamide, Clindamycine, Dapsone, Naftifine, Miconazole, Erythromycin, Terbinafine, Amitriptyline, Bisoctrizole, Benzalkonium Chloride, Chlorhexidine, Celecoxib, N,N Dimethyl 4-aminoazobenzene, Diclofenac, Doxepin, Fluconazole, Gabapentin, Ketamine, Lidocaine, Benzocaine, Metronidazole, Morphine, Nicotine, Octenidine, Octopirox. The cationic drugs can be used alone or in combination with other drugs, actives, or cationic drugs. Imiquimod is an aromatic amine, and can be provided in the form of a salt. The salt form of Imiquimod is acidic, and the pK of Imiquimod is 4.5. Imiquimod is an aromatic amine having the following structure:

Polymer Component

The cationic pharmaceutically active ingredient containing composition can include a polymer component. The polymer component can be provided as a component that exhibits a tendency to bond to skin tissue, and hold the cationic pharmaceutically active ingredient in place and allow the cationic pharmaceutically active ingredient to be released at a desired rate. When the polymer component is provided as a polymer that has a tendency to bond to skin tissues, the polymer component can be characterized as a skin bonding polymer component.

The polymer component can include a hydrophobic polymer/hydrophilic polymer adduct and can include other components. Polymer components that can be used according to the invention can include the polymer components disclosed in U.S. Pat. No. 6,756,059. The entire disclosure of U.S. Pat. No. 6,756,059 is incorporated herein by reference.

The polymer component of the composition can be, at least in part, responsible for holding or isolating the cationic pharmaceutically active ingredient and releasing the cationic pharmaceutically active ingredient at a controlled rate. The polymer component can help hold the cationic pharmaceutically active ingredient in proximity to the skin tissue once it is applied to skin tissue. By binding to skin tissue and holding on to the cationic pharmaceutically active ingredient, the polymer component can help deliver the cationic pharmaceutically active ingredient to the skin tissue to provide a desired level of activity for a desired length of time. For example, the cationic pharmaceutically active ingredient containing composition can be provided so that it adheres or binds to skin tissue for at least about one hour, and preferably at least about two hours, and holds the cationic pharmaceutically active ingredient in proximity to the skin tissue for that length of time.

The polymer component can be prepared from a topical composition precursor. The topical composition precursor can be prepared by melt processing a hydrophobic polymer composition and a hydrophilic polymer composition to provide an interaction between the hydrophobic polymer composition and the hydrophilic polymer composition. It should be understood that the phrase "melt processing" refers to mixing the hydrophobic polymer composition and the hydrophilic polymer composition under conditions that provide that the hydrophobic polymer component of the hydrophobic polymer composition and the hydrophilic polymer component of the hydrophilic polymer composition are in a fluid (i.e., liquid) state so that they sufficiently mix. When the polymers are sufficiently mixed, it is believed that an interaction forms between the hydrophobic polymer component and the hydrophilic polymer component. The melt processing temperature can be at least about 50° C. and can be at least about 70° C. to generate this interaction. In addition, the melt processing temperature can be at least about 80° C. or at least above 90° C., but should not be so high that it causes degradation of the polymers.

It is theorized that the interaction exhibited between the hydrophobic polymer component and the hydrophilic polymer component is a type of complex formation reaction, and that the complex, once formed, can be stable in water at temperatures up to 65° C. and at a pH range of 3.0 to 9.0. By stable, it is meant that the complex does not favor disassociation under these conditions, and tends to exhibit a desired shelf life. It is believed that this interaction provides the composition with an ability to become emulsified in water, exhibit a desired shelf life, and bind to skin tissue. The result of the interaction between the hydrophobic polymer component and the hydrophilic polymer component can be referred to as a hydrophobic polymer/hydrophilic polymer adduct. The term "adduct" is used to refer to the interaction between the hydrophobic polymer component and the hydrophilic polymer component. The interaction may be a form of complexing, but that is only theory. Accordingly, the term "adduct" is not meant to limit the polymer component to a particular theory of interaction. The interaction, however, provides an emulsion containing the adduct with an enhanced shelf life compared with an emulsion where an adduct has not been formed. An emulsion containing the adduct can exhibit enhanced resistance to splitting into separate phases. It has been found that an emulsion formed by simply mixing the hydrophobic polymer composition and the hydrophilic polymer composition under conditions so that the adduct is not formed results in a composition that has a greater tendency to split into separate phases.

It is believed that the interaction between the hydrophobic polymer component and the hydrophilic polymer component can be achieved more easily in the absence of water. It has been found that if the hydrophilic polymer component becomes dissolved in water before forming the complex, it can be more difficult to sufficiently mix the hydrophobic polymer component and the hydrophilic polymer component to provide the desired level of interaction. Although a convenient technique for providing the desired level of interaction between the hydrophobic polymer component and the hydrophilic polymer component is melt mixing, it is expected that other techniques can be used to achieve the desired level of interaction.

The hydrophobic polymer composition includes at least one hydrophobic polymer and can include a mixture of hydrophobic polymers. The hydrophobic polymer composition can include components having repeating pyrrolidone/alkylene groups. Exemplary polymers having repeating pyrrolidone/ alkylene groups include poly(vinylpyrrolidone/alkylene) polymers. Poly(vinylpyrrolidone/alkylene) polymers include those polymers obtained by polymerizing alkylene substituted vinylpyrrolidone. Poly(vinylpyrrolidone/alkylene) polymers can be represented by the following general formula:

wherein R represents a carbon chain such as an alkylene group and n represents the number of repeating units. The R group is preferably sufficiently long so that the polymer remains relatively water insoluble and should not be too long so that the polymer is difficult to melt process. The alkylene group can contain at least about 10 carbon atoms and can contain less than about 30 carbon atoms. The alkylene group can contain about 14 carbon atoms to about 22 carbon atoms, and can contain about 15 carbon atoms to about 19 carbon atoms.

The poly(vinylpyrrolidone/alkylene) polymers can have a molecular weight that is sufficiently high so that the polymer maintains its water insolubility but the molecular weight should not be so high that it becomes difficult to melt process the polymer. The weight average molecular weight of the poly(vinylpyrrolidone/alkylene) polymer can be between about 3,000 and about 400,000. Another way to characterize the size of the poly(vinylpyrrolidone/alkylene) polymer is by the number of repeating units (n). In the case of a poly(vinylpyrrolidone/alkylene) polymer having a weight average molecular weight of about 6,000 to about 30,000, the poly(vinylpyrrolidone/alkylene) polymer can have about 20 to about 80 repeating units, and can have about 30 to about 50 repeating units. It should be understood that repeating units refer to the residues of vinylpyrrolidone/alkylene groups.

Exemplary poly(vinylpyrrolidone/alkylene) polymers include poly(vinylpyrrolidone/1-eicosene) and poly(vinylpyrrolidone/hexadecene). Poly(vinylpyrrolidone/1-eicosene) can be referred to as PVPE and is commonly used in pharmaceutical and cosmetic preparations. An exemplary form of PVPE for use according to the invention includes about 43 to 44 repeating units in length and has a weight average molecular weight of about 17,000 and can be characterized as a paraffin-like solid. This particular PVPE is highly insoluble in water, and has an extremely low oral toxicity ($LD_{50}$>17000 mg/kg) and exhibits no demonstrable dermal toxicity. Poly(vinylpyrrolidone/1-hexadecene) can be referred to as PVPH. An exemplary form of PVPH is available as a viscous yellow liquid that is insoluble in water and has a low oral toxicity ($LD_{50}$>64000 mg/kg), has about 39 to 40 repeating units, a molecular weight of about 14,000, and exhibits no demonstrable dermal toxicity.

PVPE and PVPH differ in the length of the hydrocarbon side chain, and are used extensively in the skin care industry, usually at concentrations of less than 1% by weight, because of their ability to bind to skin. Because the skin care industry generally prefers to apply actives to skin using a water-based composition, the use of PVPE and PVPH often requires solvents, surfactants, and emulsifiers to stabilize these polymers in a water emulsion. However, many of the solvents, surfactants and emulsifiers used to stabilize PVPE and PVPH in a water emulsion lack the low dermal toxicities of PVPE and PVPH. PVPE and PVPH by themselves lack a cosmetically elegant appeal when applied directly to the skin. They tend to be sticky and greasy.

The hydrophobic polymer composition can be provided as a single poly(vinylpyrrolidone/alkylene) polymer or as a mixture of different poly(vinylpyrrolidone/alkylene) polymers. The mixture of different poly(vinylpyrrolidone/alkylene) polymers can include at least 5 wt. % of a first poly(vinylpyrrolidone/alkylene) polymer based on the weight of the hydrophobic polymer composition. The hydrophobic polymer composition can include about 5 wt. % to about 54 wt. % of the first poly(vinylpyrrolidone/alkylene) polymer. The second poly(vinylpyrrolidone/alkylene) polymer can be provided in an amount of at least about 46 wt. % and can be in a range of about 46 wt. % to 95 wt. % based on the weight of the hydrophobic polymer composition. For a hydrophobic polymer composition containing a first poly(vinylpyrrolidone/alkylene) polymer and a second poly(vinylpyrrolidone/alkylene) polymer, the mole ratio of the first polymer to the second polymer can be about 1:22 to about 1:1. When the hydrophobic polymer composition contains a mixture of different poly(vinylpyrrolidone/alkylene) polymers, the poly(vinylpyrrolidone/alkylene) polymers can be selected to provide improved properties compared to a composition having a hydrophobic polymer composition containing a single poly(vinylpyrrolidone/alkylene) polymer.

When the hydrophobic polymer composition is provided as a mixture of PVPH and PVPE, the PVPH can be provided in a range of about 46 wt. % to about 95 wt. % and the PVPE can be provided in a range of about 5 wt. % to about 65 wt. %, based upon the weight of the hydrophobic polymer composition.

The hydrophilic polymer composition can include at least one hydrophilic polymer and may include a mixture of hydrophilic polymers. The hydrophilic polymers that can be used include polymers having repeating carboxylic acid groups, hydroxyl groups, or both carboxylic acid groups and hydroxyl groups. Exemplary hydrophilic polymers that can be used according to the invention include polyacrylic acid polymers, poly(maleic acid/methylvinylether) copolymers, starch, derivatives of starch, polyvinyl alcohol, cellulose, derivatives of cellulose, carboxymethyl cellulose, cyclodextrins, dextrans, or mixtures thereof. The hydrophilic polymers should have a molecular weight that is not too high so that the hydrophilic polymer becomes difficult to process.

Polyacrylic acid polymers that can be used include those having a weight average molecular weight of at least about 50,000. Polyacrylic acid polymers that can be used include those having a weight average molecular weight between about 50,000 to about 4,000,000. The polyacrylic acid polymers can have a level of cross-linking that is less than about 1% to help provide hydrophilic properties. A general structural representation of polyacrylic acid polymers is shown below:

wherein n is the number of repeating units. The number n can be about 1,000 to about 20,000.

Poly(maleic acid/methylvinylether) copolymers that can be used can have a weight average molecular weight of at least about 50,000, and can have a weight average molecular weight of about 50,000 to about 4,000,000. The weight average molecular weight can be about 70,000 to 2,500,000. A general structural representation of poly(maleic acid/methylvinylether) copolymers is shown below:

wherein n is the number of repeating units. The number n can be about 200 to about 20,000.

Additional hydrophilic polymers that can be used include starch, derivatives of starch, polyvinyl alcohol, cellulose, derivatives of cellulose, carboxymethyl cellulose, cyclodextrins, and dextrans. The weight average molecular weight of the hydrophilic polymers is preferably sufficient to provide solubility in water but not too high to become difficult to process. Exemplary starches include amylopectin and polyglucose. Starches that can be used can have a weight average molecular weight of about 50,000 to about 20,000,000. An exemplary starch component that can be used includes *Zea Mays* starch. A derivative of starch that can be used according to the invention includes partially hydrolyzed starch. Cellulose that can be used can have a weight average molecular weight of about 50,000 to about 15,000,000. An exemplary cellulose component that can be used includes cellulose gum. Polyglucose that can be used can be characterized as low fraction polyglucose having a weight average molecular weight of about 60,000 to about 90,000, and high fraction polyglucose having a weight average molecular weight of about 90,000 to about 300,000. An exemplary low fraction polyglucose material that can be used is available under the name Dextran-70. In general, this type of polyglucose has all alpha 1-6 linkages. Starch derivatives that can be used include those starch derivatives having alpha 1-4 linkages. An example of this type of starch derivative includes cyclodextrins. Exemplary cyclodextrins that can be used include those that act to provide a cavity within the molecule large enough to contain components desirable for topical applications. Cyclodextrins that can be used can have a molecular weight of about 900 to about 1,400. Polyvinyl alcohols that can be used include those with a weight average molecular weight of about 50,000 to about 200,000.

Exemplary hydrophilic polymers that can be used include those polymers having a melting temperature that allows for melt processing without decomposition of the polymer. Exemplary poly(maleic acid/methylvinylether) copolymers that can be used include those having a melting temperature range of about 60° C. to about 65° C. and a maximum temperature range of about 80° C. to about 90° C. The melting temperature refers to the temperature at which the polymer melts, and the maximum temperature refers to the temperature at which the polymer begins to decompose. Exemplary polyacrylic acid polymers that can be used include those having a melting temperature range of about 65° C. to about 70° C. and a maximum temperature range of about 80° C. to about 90° C. Exemplary carboxymethyl cellulose polymers that can be used include those having a melting temperature range of about 55° C. to about 60° C. and a maximum temperature range of about 75° C. to about 80° C. Exemplary polyvinyl alcohol polymers that can be used include those having a melting temperature range of about 50° C. to about 55° C. and a maximum temperature range of about 65° C. to about 70° C. Exemplary starches that can be used include those having a melting temperature range of about 40° C. to about 45° C. and a maximum temperature range of about 50° C. to about 55° C. Exemplary dextrans that can be used include those having a melting temperature range of about 37° C. to about 40° C. and a maximum temperature range of about 45° C. to about 50° C. Exemplary β-cyclodextrins that can be used according to the invention include those having a melting temperature range of about 40° C. to about 45° C. and a maximum temperature range of about 65° C. to about 70° C.

The hydrophobic polymer composition and the hydrophilic polymer composition can be combined and heated to at least about 50° C. to provide a polymer melt. The composition can be heated to at least about 70° C. under mixing to form a complex between the hydrophobic and hydrophilic polymers. It should be understood that a polymer melt refers to a polymer that flows or becomes fluid or liquid when heated and is not meant to refer to a polymer that forms a liquid as a result of being dissolved in a solvent.

The complex formation step can be carried out in a relatively anhydrous environment. Once the desired level of complex formation has occurred, the composition can be hydrated with water. It has been found that the presence of water during the complex formation step can have a deleterious effect on the complex formation process. The reason for this may be that water is ionic and, as a result, can have a tendency to reduce the interaction between the hydrophobic polymer component and the hydrophilic polymer component when they are melt mixed. Accordingly, it is desirable to limit the amount of water present during the complex formation step to a level that does not significantly interfere with the complex formation step or prevent the formation of a complex. In general, this level is typically less that about 1 wt. % water. Preferably, the amount of water is limited to less that about 0.5 wt. %. It should be understood that the reference to the amount of water refers to free water.

The hydrophobic polymer composition and the hydrophilic polymer composition can be mixed together in amounts sufficient to provide a ratio of pyrrolidone groups to a combination of carboxylic acid groups and hydroxyl groups of about 1:1 to about 5:1. The ratio of the structures causing the observed interaction between the hydrophobic polymer composition and the hydrophilic polymer composition can be referred to as "functional group parity." The ratio of pyrrolidone groups to the combination of carboxylic acid groups and hydroxyl groups can be about 1.5:1 to about 3:1. In order to drive the complex formation reaction, it is desirable to provide an imbalance between the two types of groups. Accordingly, it is generally desirable to provide more of the pyrrolidone groups than the combination of carboxylic groups and the hydroxyl groups. It should be understood that the reference to a "combination of carboxylic acid groups and hydroxyl groups" refers to the total amount of carboxylic groups and hydroxyl groups present but does not require the presence of both carboxylic groups and hydroxyl groups. For example, the value of the combination of carboxylic acid groups and hydroxyl groups can be determined for a composition that contains only carboxylic acid groups. Similarly, the value can be determined for a composition that contains only hydroxyl groups.

During the complex formation step, the amounts of hydrophobic polymer composition and hydrophilic polymer composition can be characterized on a weight percent basis. For example, about 2 wt. % to about 28 wt. % hydrophilic polymer composition and about 72 wt. % to about 98 wt. % hydrophobic polymer composition can be combined to provide for complex formation. About 8 wt. % to about 25 wt. % hydrophilic polymer composition and about 72 wt. % to about 95 wt. % hydrophobic polymer composition can be combined to form the complex. During the complex formation step, the amount of water available in the composition can be less than about 1 wt. %. Although the complex forming composition can be relatively anhydrous, it is expected that the amount of water can be between about 0.3 wt. % and about 1.0 wt. %. It should be understood that the amount of water refers to free water.

Once the hydrophobic polymers and the hydrophilic polymers have sufficiently reacted or interacted to form a complex, water can be added to the composition to provide a stable aqueous composition that can be relatively easily further hydrated. It has been found that the first hydration of the topical composition precursor is the most difficult hydration step because of the need to control the conditions of hydration. After the first hydration to a water content of at least about 30 wt. %, it is expected that further hydrations to higher water contents are relatively easy and can be accomplished by simply mixing the composition with water. Accordingly, the amount of water provided in the composition when made available as a concentrate for shipment is preferably between about 30 wt. % and about 45 wt. %. When the composition includes about 30 wt. % to about 45 wt. % water, it is expected that the composition can include about 3 wt. % to about 10 wt. % hydrophilic polymer composition and about 30 wt. % to about 50 wt. % hydrophobic polymer composition.

Water can be added to the relatively anhydrous composition by mixing water and the relatively anhydrous composition at a temperature and for a time sufficient to allow the composition to become hydrated without losing significant amounts of interaction between the hydrophobic polymer composition and the hydrophilic polymer composition. The relatively anhydrous composition can be hydrated by heating to at least 60° C. and adding water while mixing. The composition can be heated to at least about 65° C. and to at least about 70° C. An exemplary temperature range is about 65° C. to about 80° C.

The relatively anhydrous composition can be referred to as the topical composition precursor and generally refers to the hydrophobic polymer/hydrophilic polymer adduct containing less than about 1.0 wt. % water if any water is present. The polymer component for the composition can refer to a composition that contains only the hydrophobic polymer/hydrophilic polymer adduct, and it can refer to a composition wherein the hydrophobic polymer/hydrophilic polymer adduct is diluted with water. In general, it is desirable to have a sufficient amount of water in the polymer component that allows one to formulate the polymer component into the cationic pharmaceutically active ingredient containing composition according to the invention. If there is too little water in the polymer component, it may become difficult to formulate the composition. For example, the polymer component can contain water in an amount of up to about 95 wt. % and may contain water in an amount up to about 97 wt. %. The polymer component can have a water concentration of about 30 wt. % to about 45 wt. %.

Additional components can be added to the hydrophobic polymer/hydrophilic polymer adduct. For example, it may be desirable to add a component that helps stabilize the hydrophobic polymer/hydrophilic polymer adduct, and to help preserve and/or maintain the composition.

The cationic pharmaceutically active ingredient containing composition can include the polymer component or polymer adduct in an amount sufficient to provide desired bonding properties of the composition. For example, the cationic pharmaceutically active ingredient containing composition can include at least about 2 wt. % of the polymer component or polymer adduct. In addition, the composition can contain at least 3 wt. % of the polymer component or polymer adduct, and preferably at least about 4 wt. % of the polymer component or polymer adduct. In addition, the cationic pharmaceutically active ingredient containing composition can include a sufficient amount of the polymer component or polymer adduct to desirably protect the cationic pharmaceutically active ingredient from degradation and allow the cationic pharmaceutically active ingredient containing composition to deliver the cationic pharmaceutically active ingredient to skin tissue upon application of the cationic pharmaceutically active ingredient containing composition to the skin tissue. The cationic pharmaceutically active ingredient containing composition can contain the polymer component in an amount of less than about 20 wt. %, and preferably in an amount of less than about 15 wt. %. Exemplary ranges of polymer component include about 2 wt. % to about 20 wt. %, about 4 wt. % to about 15 wt. %, and about 5 wt. % to about 8 wt. %.

An exemplary polymer component that can be used is available under the name Invisicare™ C-5 composition from Skinvisible Pharmaceuticals, Inc. Invisicare™ C-5 composition contains a mixture of poly(vinylpyrrolidone/eicosene) and poly(vinylpyrrolidone/hexadecene), and carboxymethyl cellulose.

Water

The cationic pharmaceutically active ingredient containing composition can include water in an amount sufficient to allow the composition to be applied to skin tissue while providing the desired coverage over the skin tissue. The water component can be provided as deionized water, filtered water, distilled water, reverse osmosis water, or tap water. In the event that the water includes hardness or other components, it may be desirable to include builders, sequestrants, and chelating agents to handle the water hardness. In general, the composition can include at least about 50 wt. % water. In addition, it is expected that if there is too much water, the emulsion might become unstable. In general, the amount of water in the composition can be less than about 95 wt. %. The amount of water in the composition can be about 65 wt. % to about 93 wt. %.

Long Chain Organic Acid

The cationic pharmaceutically active ingredient containing composition can include a long carbon chain containing organic acid. A long carbon chain containing organic acid can be characterized as an organic acid having a carbon chain that is sufficiently long to help compatibilize or contain the cationic pharmaceutically active ingredient with the polymer component. While not being bound by theory, it is generally understood that the polymer component in the hydrated composition forms relatively small micelles having a hydrophobic exterior. The long carbon chain on the organic acid compatibilizes with the hydrophobic exterior of the micelles formed by the polymer component, and the acid portion can attract or hold onto the cationic pharmaceutically active ingredient by, for example, ionic bonding. The long carbon chain containing organic acid can be referred to as the long chain organic acid or even more simply as the organic acid.

If the carbon chain on the long carbon chain organic acid is too short, it may be difficult for the long chain organic acid to interact or combine with the polymer component or adduct. For example, the long chain organic acid can have a carbon chain that is at least about 8 carbon atoms long, and can have a carbon chain that is at least about 10 carbon atoms long. If the carbon chain on the long chain organic acid is too long, it may be difficult to process the organic acid. For example, the long chain organic acid can have a carbon chain that is less than about 22 carbon atoms long, and can have a carbon chain that is less that about 20 carbon atoms long. The long chain organic acid can have a carbon chain of about 10 carbon atoms to about 18 carbon atoms. In addition, the long chain organic acid can have a carbon chain of about 12 carbon atoms to about 16 carbon atoms. Exemplary long chain organic acids that can be used include lauric acid, stearic acid, palmitic acid, myristic acid, and mixtures thereof.

The long chain organic acid can be provided as a component having a single acidic group or multiple acidic groups. Exemplary long chain organic acids that contain multiple acidic groups include those characterized as di-acids and tri-acids. Bonding or other interaction can occur between each acidic group of the long chain organic acid and molecules of cationic pharmaceutically active ingredients.

The composition can contain the long chain organic acid in an amount sufficient to assist with the stabilization or controlled release of the cationic active ingredient. The amount of the long chain organic acid can be selected depending upon the amount of the cationic active ingredient provided in the composition. If there is a very small amount of the cationic active ingredient, it may be possible to use a relatively small amount of the long chain organic acid in order to compatibilize the cationic active within the composition. For example, the long chain organic acid can be provided in the composition in an amount of at least about 0.05 wt. %. In addition, the amount of the long chain organic acid in the composition can be provided in an amount of at least about 0.5 wt. %. By way of example, the composition can contain about 0.5 wt. % to about 10 wt. % of the long chain organic acid, and can contain about 1.0 wt. % to about 8 wt. % of the long chain organic acid.

The long chain organic acid can be selected depending upon the cationic active ingredient that is provided in the cationic pharmaceutically active ingredient containing composition. In order to optimize the ability of the long chain organic acid to compatibilize the cationic active into the composition, the long chain organic acid can be selected as a long chain organic acid having a pK value that is sufficiently close to the pK value of the cationic active ingredient. The pK values are "sufficiently close" when, for example, they are within 2 pH units of each other. Preferably, the pK values of the long chain organic acid and the cationic active ingredient are within about 1 pH unit, and more preferably within about 0.5 pH unit. By way of example, Imiquimod has a pK value of 4.5. Lauric acid is an exemplary long chain organic acid having a pK value of 5.3. Because these pK values are within 1 pH unit, it is expected that lauric acid would serve as a desirable long chain organic acid for compatibilizing Imiquimod.

In order to create an environment where an attraction exists between the acidic group on the long chain organic acid and the cationic pharmaceutically active ingredient, it is desirable for the composition to have a pH that is about equivalent to the pK of the cationic pharmaceutically active ingredient. In general, if the pH of the composition is too high, then the result is a deprotonating of the long chain organic acid and the cationic active ingredient which has tendency to result in a loss of ionic interaction between the long chain organic acid and the cationic active ingredient. Similarly, if the pH of the composition is too low, the result is a protonating of the long chain organic acid and the cationic active ingredient resulting in a tendency toward a loss of ionic interaction between the long chain organic acid the cationic active ingredient. If there is a loss of ionic interaction between the long chain organic acid and the cationic active ingredient, there is a tendency for a loss of ability of the composition to hold the cationic active ingredient and thereby control the release of the cationic active ingredient. As a result, it is generally desirable for the composition to have a pH that is about equivalent to the pK of the cationic pharmaceutically active ingredient. By "about equivalent," it is meant that the difference between the pH of the composition and the pK of the cationic active ingredient is within about 2 pH units, preferably within about 1 pH unit, and more preferably within about 0.5 pH unit. Because different cationic active ingredients may have different pK values, the pH of the composition can be selected so that it is within about 2 pH units of the pK of the cationic active ingredient in order to maximize the amount of cationic active ingredient held by the composition. The composition can be provided having a pH that is within about 1 pH unit of the pK of the cationic active ingredient, and can be provided having a pH that is within about 0.5 pH unit of the pK of the cationic active ingredient. Alternatively, the composition can be selected so that it has a pH that is within about 2 pH units of the pK of the long chain organic acid. In addition, the pH of the composition can be selected so that it has a pH that is within about 1 pH unit of the pK value of the long chain organic acid, and can be selected so that it has a pH that is within about 0.5 pH unit of the pK value of the long chain organic acid. By way of example, a composition containing Imiquimod as the active ingredient (pK value of about 4.5) can have a pH value in the range of about 2.5 to about 6.5, and preferably about 3.5 to about 5.5, in order to optimize the amount of Imiquimod held by the composition. The pH value of the composition can be selected based on the physiological activity of the composition based upon that pH value. For example, if the pH value of the composition is too low, the composition may have a tendency to irritate or cause the skin to peel off. In certain circumstances, depending upon the active ingredient, it may be desirable for the composition to have a sufficiently low pH that it causes the skin to peel off. For many types of compositions, however, it is expected that the pH of the composition should be at least about 3.5 in order to avoid an adverse physiological effect on the skin tissue to which the composition is applied. Furthermore, it should be understood that if the pH of the composition is too different from the pK of the cationic active and the pK of the long chain organic acid, there may exist an undesired level of protonating or deprotonating of the cationic active and/or the long chain organic acid. Accordingly, although a permissible 2 pH unit range is identified, it may be desirable to provide a smaller range.

pH Adjusting Agent

The composition can include pH adjusting agents, buffering agents, or neutralizing agents to provide the composition with a pH that helps stabilize the cationic pharmaceutically active ingredient. Exemplary pH adjusting agents that can be used include sodium hydroxide, potassium hydroxide, triethanolamine, acetic acid, propionic acid, citric acid, succinic acid, and mixtures thereof.

The polymer component of the lotion, cream, gel, or liquid may be at least in part responsible for reducing the irritability of the composition. For example, it is believed that the polymer component may help reduce irritation of skin tissue. The composition can be provided without any pH modifier, if desired. In general, however, a buffering agent is incorporated into the composition to help control the pH of the composition. Furthermore, the buffering agent is typically selected as a buffering agent that is compatible with skin issue or that does not harm skin tissue.

It is desirable for the composition to have a pH that is within about 2 pH units of the pK value of the cationic active ingredient or within about 2 pH units of the pK value of the long chain organic acid in order to maximize the ability of the composition to hold onto the cationic active ingredient and control the release of the cationic active ingredient. Preferably, the composition has a pH in the range of about 1 pH unit of the pK value of the cationic active ingredient or in the range of about 1 pH unit of the pK value of the long chain organic acid. The composition can have a pH in the range of about 0.5 pH unit of the pK value of the cationic active ingredient or within about 0.5 pH unit of the pK value of the long chain organic acid.

Release Agent

The cationic pharmaceutically active ingredient containing composition can include a release agent to assist with the sustained release of the cationic pharmaceutically active component over a prolonged period of time. The release agent can be provided as a surfactant. A surfactant can additionally be present to help maintain the cationic pharmaceutically active ingredient containing composition as an emulsion. In general, an emulsion refers to a composition that resists phase separation after sitting at room temperature for a couple of months. In general, it is expected that the cationic pharmaceutically active ingredient containing composition can be stored in a warehouse or in a storage closet for at least two months and can remain as an emulsion during that two month period. Preferably, the composition can remain as an emulsion for at least one year or at least two years. The ability of the cationic pharmaceutically active ingredient containing composition to remain as an emulsion can be tested according to an accelerated stability test where the composition is held at 40° C. for 120 days. It is expected that this accelerated stability test for 120 days roughly corresponds to a period of about two years at room temperature. In general, it is expected that the composition can remain as an emulsion after sitting for two years at room temperature.

Exemplary surfactants that can be used as the surfactant component include nonionic surfactants that help stabilize the emulsion and provide a generally even distribution of the cationic pharmaceutically active ingredient containing component. Exemplary nonionic surfactants that can be used include glycerol stearate such as glycerol monostearate, polysorbate such as that available under the name Tween 80, polyoxyethylene stearate. In addition, mixtures of nonionic surfactants can be included including mixtures of polysorbate and glycerol stearate. An additional nonionic surfactant that can be used includes an ethoxy surfactant, a propoxy surfactant, or an ethoxy/propoxy surfactant. An exemplary ethoxy/propoxy surfactant includes a 10 carbon chain and 9 PO/EO surfactant available under the name Lutensol XP-90 from BASF. Additional nonionic surfactants include sorbitan monolaurate and sorbitan monostearate. Additional surfactants that can be used include those that are generally characterized as Pluronic surfactants such as poloxamers. An exemplary surfactant that can be used is Pluronic L44NF from BASF.

It is believed that anionic surfactants may be useful as part of the surfactant component. In general, it is expected that anionic surfactants have a greater tendency to cause irritation to skin tissue.

The cationic pharmaceutically active ingredient containing composition can include an amount of surfactant component sufficient to provide the composition with a desired emulsion stability and sufficiently low viscosity without foaming. The amount of the surfactant component in the composition, can be about 0.5 wt. % to about 6 wt. %, and can be about 1 wt. % to about 5 wt. %. It should be understood that the composition can be provided without any surfactant component, if desired.

The composition can contain a release agent to assist with the sustained release of the cationic pharmaceutically active ingredient over a prolonged period of time. A sustained release of the cationic pharmaceutically active ingredient refers to a release, over the time period, wherein the release provides desired properties. In general, it is desirable for the cationic pharmaceutically active ingredient containing composition to provide a relatively consistent release of the cationic pharmaceutically active ingredient component after application of the composition to skin tissue. A relatively consistent release can be characterized as a release rate at one hour that is within about 50% of the release rate at 30 minutes. In addition, a relatively consistent release rate can be characterized as a release rate at two hours that is within about 50% of the release rate at 30 minutes. Preferably, these release rates can be provided within about 25%, and more preferably can be provided within about 15%.

At least two advantages can be obtained by providing a sustained release rate or a relatively constant release rate over a prolonged period of time. For example, by providing a sustained release of the cationic pharmaceutically active ingredient over a prolonged period of time, it is possible to prolong the pharmaceutical efficacy of the cationic pharmaceutically active ingredient containing composition after application to skin tissue. By prolonging the pharmaceutical efficacy of the cationic pharmaceutically active ingredient containing composition, it is expected that enhanced performance can be achieved. Furthermore, by controlling the release of the cationic pharmaceutically active ingredient so that it is not released at one instant in time, it is possible to reduce or minimize skin irritation. Many cationic pharmaceutically active ingredients have a tendency to cause skin irritation if provided at a concentration that is too high. By controlling the release of the cationic pharmaceutically active ingredient, it is possible to reduce the tendency of the cationic pharmaceutically active ingredient to cause skin irritation because too much of it is released at one time.

Thickener

Thickeners that can be incorporated into the composition include those components that thicken or increase the viscosity of the composition so that the composition can be readily applied to skin. Thickeners that can be used in the composition include those components often referred to as viscosity controlling agents.

Exemplary thickeners or viscosity controlling agents that can be provided in the hand disinfecting composition include cellulose gum, alkane triols; acrylates; substituted celluloses such as hydroxy ethyl cellulose, carboxymethyl cellulose, methylcellulose, and hydroxypropyl cellulose; cetyl alcohol; gums such as natural gums or synthetic gums; long chain alcohols such as those having about 9 to about 24 carbon atoms; polyglycols such as polyethylene glycols, polypropylene glycols, polybutylene glycols, polyethylene propylene glycols, or mixtures thereof; waxes such as natural waxes or synthetic waxes; hydrogenated oils; glycol esters; fatty acid esters; long chain acids; acid amides; silicates; and mixtures thereof. Exemplary thickeners that can be used is hydroxyethyl cellulose. An exemplary thickener that can be used is a polyacrylic acid thickeners available under the name Carbopol from Lipscomb.

The composition may or may not include a thickener. When the composition includes a thickener, the thickener can be provided in an amount that provides the desired level of thickening. The composition can include a thickener in an amount of least about 0.1 wt. % and can include a thickener in an amount of at least about 0.4 wt. %. In addition, the thickener can be provided in an amount of less than about 4 wt. %, and can be provided in an amount of less than about 2 wt. %.

Emollient

The composition can include an emollient for improving the texture of the composition. An emollient is an oleaginous or oily substance which helps to smooth and soften the skin, and may also reduce its roughness, cracking or irritation. Exemplary suitable emollients include mineral oil, having a viscosity in the range of 50 to 500 centipoise (cps), lanolin oil, coconut oil, cocoa butter, olive oil, almond oil, macadamia nut oil, synthetic jojoba oils, natural sonora jojoba oils, safflower oil, corn oil, liquid lanolin, aloe vera, cottonseed oil, and peanut oil.

Other suitable emollients include squalane, castor oil, polybutene, odorless mineral spirits, sweet almond oil, avocado oil, clophyllum oil, ricin oil, vitamin E acetate, olive oil, linolenic alcohol, coconut oil, oleyl alcohol, the oil of cereal germs such as the oil of wheat germ, isopropyl palmitate, isopropyl myristate, hexadecyl stearate, butyl stearate, decyl oleate, acetyl glycerides, the octanoates and benzoates of ($C_{12}$-$C_{15}$) alcohols, the octanoates and decanoates of alcohols and polyalcohols such as those of glycol and glycerol, ricin oleates of alcohols and poly alcohols such as those of isopropyl adipate, hexyl laurate and octyl dodecanoate.

Other suitable emollients which are solids or semi-solids at room or ambient temperatures may be used in amounts sufficient to provide liquid topical compositions. Such solid or semi-solid cosmetic emollients include hydrogenated lanolin, hydroxylated lanolin, acetylated lanolin, petrolatum, isopropyl lanolate, butyl myristate, cetyl myristate, myristyl myrislate, myristyl lactate, cetyl alcohol, isostearyl alcohol and isocetyl lanolate. Exemplary emollients include stearic acid, stearyl alcohol, palmitic acid enters natural and synthetic esters such as coconut oil.

The cationic pharmaceutically active ingredient containing composition can include the emollient in an amount sufficient to provide a silky feel. An exemplary range of the emollient in the composition can be at least about 0.5 wt. %. In addition, the composition can include an emollient in an amount of less than about 3 wt. %. It should be understood that the emollient is an optional component of the composition. The cationic pharmaceutically active ingredient containing composition can be provided without an emollient, if desired.

Moisturizer

The composition can include a moisturizer to provide a desired moisturizing effect to skin tissue. The moisturizer can be provided as a humectant. In general, a humectant is a moistening agent that promotes retention of water due to its hydroscopic properties. Exemplary humectants include glycerine, polymeric glycols such as polyethylene glycol and polypropylene glycol, and sorbitols such as sorbitol solution, pyrrolidone carboxylic acid, urea, or mixtures thereof. The composition can be provided without a moisturizer.

When the cationic pharmaceutically active ingredient composition includes a moisturizer, it can be included in an amount of at least about 0.5 wt. %. In addition, the composition can include a moisturizer in an amount of less than about 5 wt. %.

An additional component that can be provided as part of the composition is a skin protectant. An exemplary protectant is allantoin that is available as a skin protectant and esthetic agent.

Preservatives

The composition can include preservatives for prevention of bacterial, fungal, and/or yeast contamination. Exemplary preservatives that can be used in the hand disinfecting composition include phenoxyethanol, benzoic acid, derivatives and salts of benzoic acid, parabens, oxazolidines, chlorinated aromatic compounds and phenols, hydantoins, cresols and derivatives, imiazolindinyl urea, iodopropanol butylcarbamate, sulfites, and bisulfites. The composition can include any of the preservatives commonly used or known to be suitable for topically applied compositions. Exemplary commercially available preservatives include liquid Germal Plus (diazolidinyl urea and iodopropynyl butylcarbamate) and Germaben 11 (diazolidinyl urea and methylparaben and propylparaben).

The composition can be formulated without a preservative. It is expected that the preservative will increase the shelf life of the composition by reducing or preventing the growth of bacteria, fungus, and/or yeast. When the composition includes a preservative, the preservative is preferably provided in an amount sufficient to provide a desired level of protection from growth of bacteria, fungus, and/or yeast.

In general, for most preservatives, it is expected that the amount of preservative can be provided at a level of about 0.1 wt. % to about 1.0 wt. %, and can be provided at a level of about 0.2 wt. % to about 0.5 wt. %, based on the weight of the composition.

Antioxidants

The composition can include antioxidants to help increase the shelf life of the composition and to provide desired properties when applied to skin tissue. Exemplary antioxidants that can be used include vitamins such as vitamin E, vitamin E acetate, vitamin C, and vitamin D, and derivatives thereof. Exemplary antioxidants include α-tocopherols which can be characterized as natural or synthetic Vitamin E. Additional exemplary antioxidants include propyl, octyl and dodecyl esters of gallic acid, butylated hydroxyanisole (BHA) (usually as a mixture of ortho and meta isomers), butylated hydroxytoluene (BHT), and nordihydroguaiaretic acid, and alkylated parabens such as methylparaben and propylparaben.

The composition can be formulated without an antioxidant. When the composition includes an antioxidant, the antioxidant can be provided in an amount that provides antioxidant properties in the composition. In general, it is expect that the antioxidant can be provided in an amount of about 0.2 wt. % to about 2 wt. %, and can be provided in an amount of about 0.7 wt. % to about 1.5 wt. %, based on the weight of the composition. In the case of vitamin E, it is expected that the vitamin E can be included in the composition in an amount of about 0.1 wt. % to about 1 wt. %, and can be included in an amount of about 0.3 wt. % to about 0.8 wt. %.

Chelating Agents

Chelating agents are substances used to chelate or bind metallic ions with a certain heterocyclic ring structure so that the ion is held by chemical bonds from each of the participating rings. Suitable chelating agents include ethylene diaminetetraacetic acid (EDTA), EDTA trisodium, EDTA tetrasodium, calcium disodium edetate, EDTA trisodium, EDTA tetrasodium and EDTA dipotassium. One or more chelating agents can optionally be included in the emulsion in amounts ranging from about 0.001 to about 0.1 weight percent. It should be appreciated that the composition can be provided without a chelating agent.

Fragrances

Fragrances are aromatic compounds which can impart an aesthetically pleasing aroma to the composition. Typical fragrances include aromatic materials extracted from botanical sources (i.e. rose petals, gardenia blossoms, jasmine flowers, etc.) which can be used alone or in any combination to create essential oils. Alternatively, alcoholic extracts may be prepared for compounding fragrances. One or more fragrances can optionally be included in the composition in an amount ranging from about 0.001 to about 10 weight percent, preferably about 0.05 to about 5 percent. It should be appreciated that the composition can be provided without a fragrance.

Carriers, Diluents, and Excipients

The composition may also include non-toxic, pharmaceutically and dermatologically acceptable carriers, diluents and excipients, suitable for topical application, as are well known, see for example Merck Index, Merck & Co., Rahway, N.J., Bioreversible Carriers in Drug Design, Theory and Application, Roche (ed.) Pergamon Press, (1987), Gilman et al., (eds) (1990) Goodman and Gilman's: The Pharmacological Bases of Therapeutics, 8th Ed., Pergamon Press, Novel Drug Delivery Systems, 2nd Ed., Norris (ed.) Marcel Dekker Inc., (1989), and Remington's Pharmaceutical Sciences. For standard dosages of conventional pharmacological agents, see, e.g., Physicians Desk Reference (1997 Edition); and American Medical Association (1997) Drug Evaluations (Subscriptions).

The cationic pharmaceutically active ingredient containing composition can be applied to skin tissue as a result of applying the composition as a cream or lotion to the skin tissue, and rubbing onto the skin tissue. The action of rubbing may include gentle rubbing or vigorous rubbing. Although the composition is sometimes characterized as having a binding or almost adhesive property with respect to skin tissue, the composition is not the type of composition that one would consider to be an adhesive that holds two substrates together such as, for example, a hot melt adhesive.

Because the cationic pharmaceutically active ingredient containing composition can bind cationic active ingredients therein, the release of the cationic active ingredient can take place over time. In contrast, many currently available compositions release the active ingredient almost instantaneously. As a result, the dose of the active ingredient from these compositions that release almost instantaneously may be too great at one time and too low soon thereafter. Furthermore, the release of a high dosage may cause skin irritation. By providing a prolonged release of the active ingredient over a period of time, the efficacy of the drug can be improved. The ability of the composition to bind the cationic active ingredient and provide a gradual or sustained release over time can be demonstrated by a two hour release from a nylon membrane property as described in Example 1. The cationic pharmaceutically active ingredient containing composition can provide a two hour release from a nylon membrane property of less than 80%. If desired, the composition can provide a two hour release from nylon membrane property of less than 50%. It is expected that a composition that does not bind the active ingredient will provide a two hour release from a nylon membrane property of greater than 90%.

Example 1

Exemplary organic acids are identified in Table 1. Three of the acids (citric acid; dodecanoic acid; and succinic acid) have more than one carboxylic acid group. Organic acids having more than one carboxylic acid group can be used to form dimeric or trimeric salts.

TABLE 1

|  | Molecular Weight | Weight Ratio of Acid/Imiquimod | $pK_1$ | $pK_2$ | $pK_3$ |
|---|---|---|---|---|---|
| Citric Acid | 192.16 | 0.26 | 3.13 | 4.76 | 6.39 |
| Stearic Acid | 284.49 | 1.18 | 7.0 | | |
| Benzoic Acid | 122.12 | 0.51 | 4.21 | | |
| Lauric Acid | 200.32 | 0.83 | 5.3 | | |
| Dodecandioic | 230.30 | 0.96 | 4.5 | 4.5 | |
| Succinic Acid | 118.49 | 0.49 | 4.16 | 5.61 | |
| Propionic Acid | 74.08 | 0.31 | 4.88 | | |
| Acetic Acid | 60.05 | 0.25 | 4.76 | | |
| Gluconic Acid | 196.00 | 0.82 | 3.86 | | |

Figure 1:
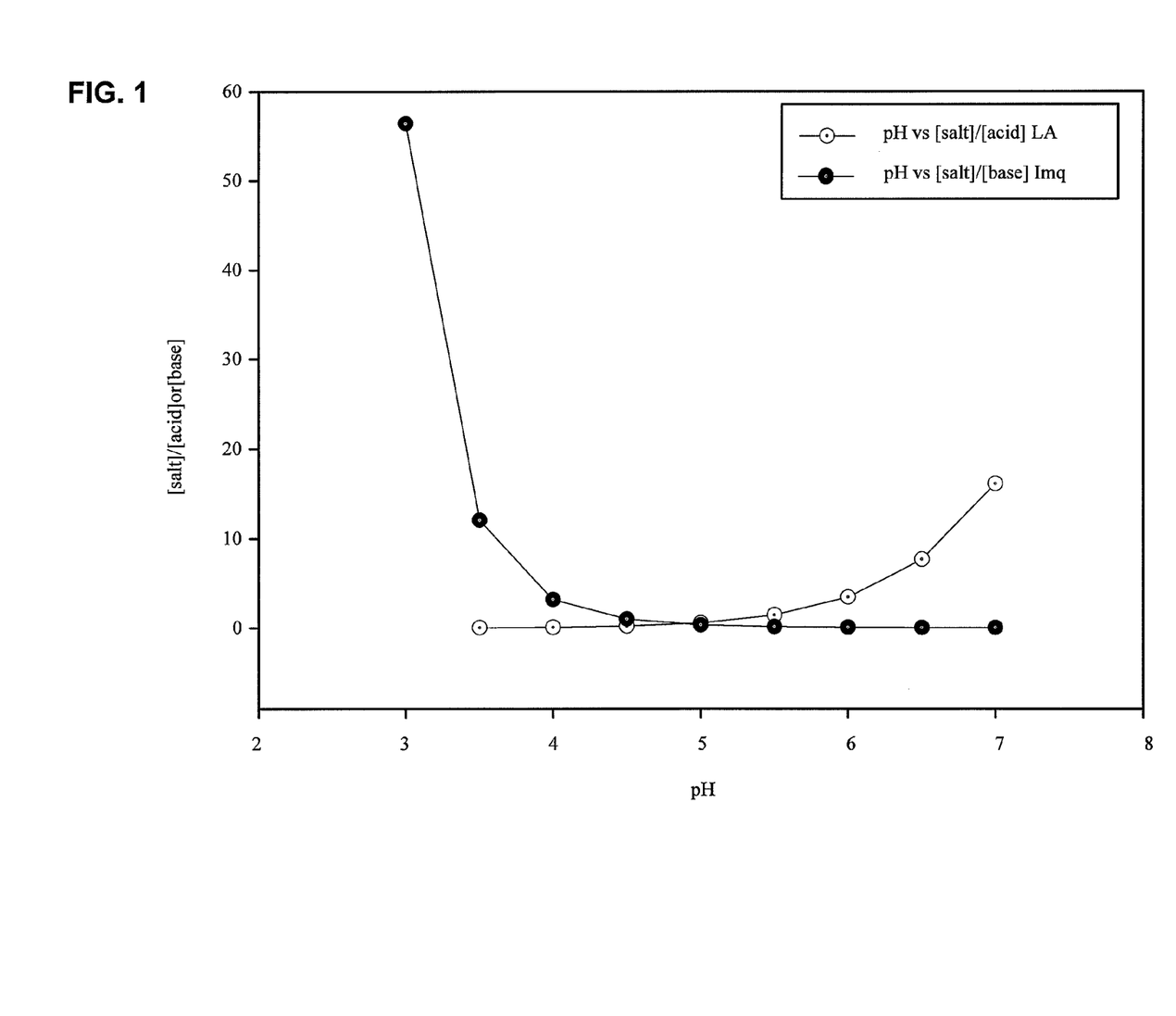
FIG. 1 is a graph showing concentration versus pH for Imiquimod and lauric acid.

A graph showing the ratio of salt to acid or base concentration versus pH for Imiquimod and lauric acid is present in FIG. 1. According to FIG. 1, the two pH curves cross just below a pH of 5. Laurie acid has a pK of 5.3, and Imiquimod has a pK of 4.5. Half of each is in its salt form at the respective pKs.

Figure 2:
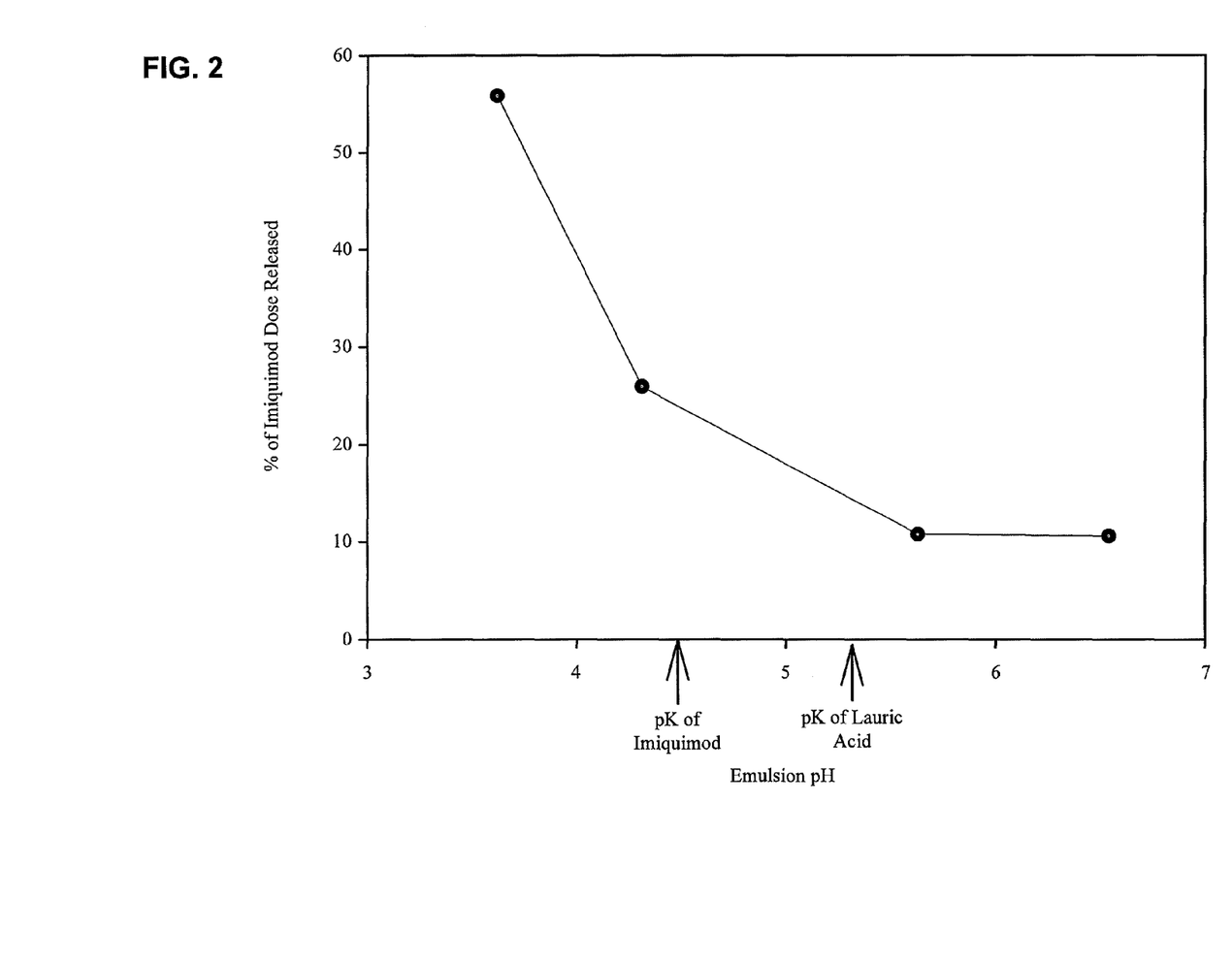
FIG. 2 is a graph showing the percent of Imiquimod dose released versus pH.

If Imiquimod can be mixed with a polymer component to form a composition that contains an equimolar amount of lauric acid to provide a system that can deliver a specific amount cationic of drug, the level of cationic drug released by the composition can be controlled by the pH of the composition. The results are shown in the graph presented in FIG. 2. FIG. 2 shows that the release of Imiquimod predicted is substantiated. The amount of the drug released follows a curve very close to the theoretical titration curve presented in FIG. 1.

However, very low pH ranges (<3.5) can be damaging to skin. For example, α-hydroxy acids are used extensively in cosmetic products as chemical skin peals. This is not a desirable effect for a drug such as Imiquimod. Exfoliation of the skin increases the permeability of the skin, and would act to increase the undesirable side effects of the drug. For this reason, it is desirable to include a pH-buffering agent in the formulation to stabilize the pH at a relatively constant value. Two acids from Table 1 offer broad pH range control. They are citric acid and succinic acid that can buffer in the pH ranges of 3 to 7, and 4 to 6 respectively. Both of these acids are normal metabolic intermediates in oxidation processes of living cells, from bacterial to mammalian. These buffering agents also have the ability to form salts with Imiquimod to either sequester or release the drug. The number of molecules of Imiquimod each of these acids will form salts with is pH dependent.

The data presented here, used in conjunction with the hydrophilic/hydrophobic polymer complexes, demonstrates a system that can control the delivery of cationic drugs/active ingredients such as Imiquimod.

An exemplary lotion for topical application can be formulated that utilizes Imiquimod as a cationic pharmaceutically active ingredient. An exemplary lotion is provided in Table 2.

TABLE 2

Lotion

| component | Wt. % |
|---|---|
| skin bonding polymer component (polymer base C5 from Skinvisible Pharmaceuticals, Inc.) | 8.0 |
| cationic active ingredient (Imiquimod) | 3.0 |
| long chain organic acid (lauric acid) | 2.5 |
| water | 80.95 |
| thickener (hydroxyethyl cellulose) | 1.0 |
| nonionic surfactant (Polysorbate 60) | 1.0 |

TABLE 2-continued

| Lotion | |
| --- | --- |
| component | Wt. % |
| sequestering agent (EDTA) | 0.5 |
| nonionic surfactant (Pluronic L44) | 0.8 |
| emollient (coconut oil) | 2.0 |
| buffer (citric acid) | 0.3 |
| preservative (phenoxyethanol) | 0.5 |

The percent of Imiquimod released after two hours is determined by applying the composition containing Imiquimod to a cleaned, hydrophilic nylon membrane, immersing the membrane in deionized water, and then measuring the amount of Imiquimod in the water. The composition can be applied to the cleaned, hydrophilic nylon membrane at an average load of about 200-300 mg. wet weight and then dried and weighed. The loaded membrane is then placed face down in a beaker containing 9 ml. deionized water. After two hours, the membrane is dried and weighed. Supernatents from the water exposure are diluted to 10 ml. and analyzed for total active ingredient released. For certain actives, the dry membrane can be extracted with solvent to determine the total amount of active ingredient remaining bound to the membrane. It is observed that, when compared to human skin, binding to human skin is more favorable compared with binding to the hydrophilic nylon membrane, and that the results are comparable.

Example 2

An exemplary cationic pharmaceutically active ingredient containing composition was prepared in the form of a cream. The composition is identified in Table 3.

TABLE 3

| Cream | |
| --- | --- |
| component | Wt. % |
| Skin bonding polymer component (polymer base C5 from Skinvisible Pharmaceuticals, Inc.) | 8.0 |
| cationic active ingredient (Imiquimod) | 3.0 |
| long chain organic acid (lauric acid) | 2.50 |
| water | 80.45 |
| thickener (hydroxyethyl cellulose) | 1.00 |
| nonionic surfactant (Polysorbate 60) | 1.00 |
| sequestering agent (EDTA) | 0.05 |
| nonionic surfactant (Pluronic L44NF) | 0.80 |
| emollient (coconut oil) | 2.0 |
| buffer (citric acid) | 0.70 |
| preservative (phenoxyethanol) | 0.50 |

The pH of the composition reported in Table 3 is 4.65. The release of Imiquimod from the composition after two hours was measured as 40% by the technique described in Example 1.

Example 3

Figure 3:
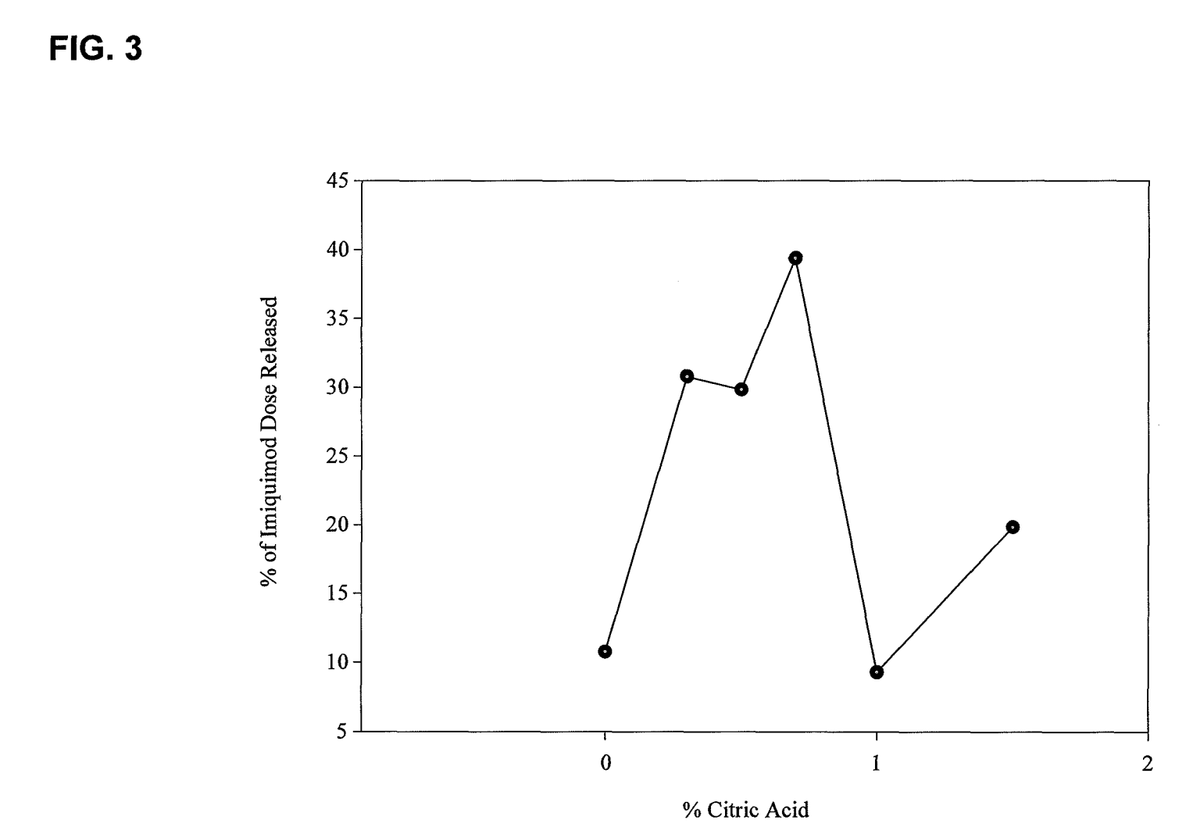
FIG. 3 is a graph showing the percent of Imiquimod dose released versus percent citric acid.

Various compositions were prepared based upon the composition shown in Table 3. The amount of citric acid was varied from 0 wt. % to 1.5 wt. %. The release of Imiquimod was measured after two hours by the technique described in Example 1. The results are presented in FIG. 3.

Figure 4:
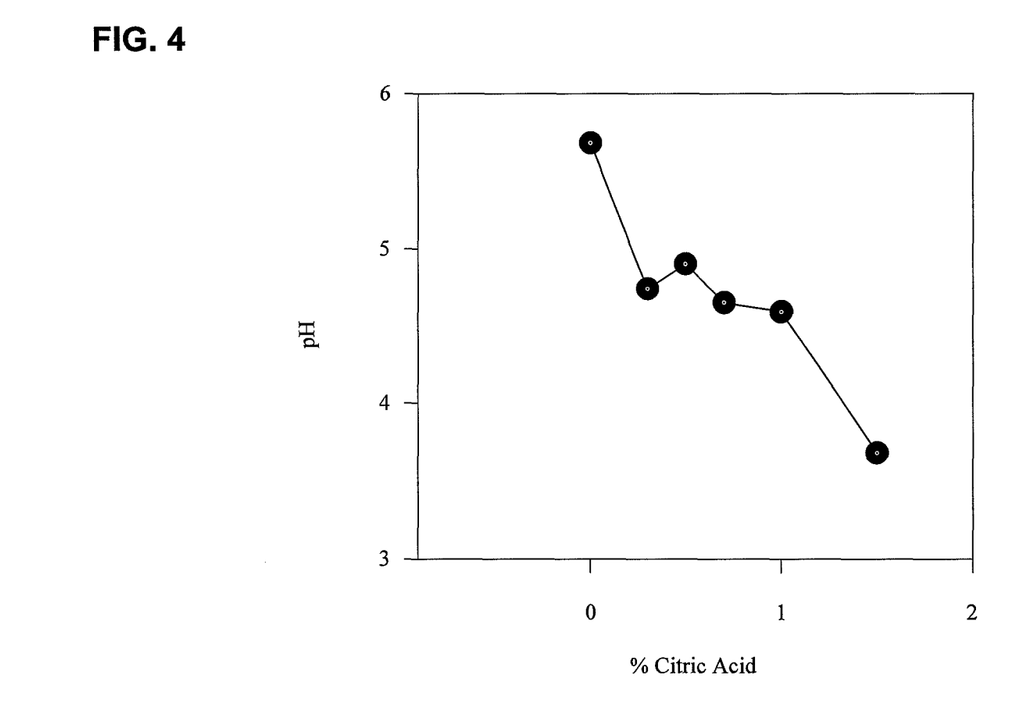
FIG. 4 is graph showing the composition pH versus percent citric acid.

FIG. 4 show a graph of pH of the composition at varying levels of citric acid ranging from 0 wt. % citric acid to about 1.5 wt. % citric acid. It can be seen from FIG. 3 that the greatest release of Imiquimod occurred at a pH of about 4.5. At pH values greater than 5 and at pH values less than 4, the composition released a lesser amount of Imiquimod. One theory explaining this is that at higher and lower pH values for the composition, a lesser amount of cationic active ingredient is compatibilized with the composition.

Example 4

The concentrations of acid and salt forms for species form the composition reported in Table 3 are shown in the table below at a pH of 4.65. Calculations are by the Henderson-Hasselbalch equation.

TABLE 4

| Component | pH | pK | pH/pK | [salt]/[acid] | [Acid Form] | [Salt Form] | Charge |
| --- | --- | --- | --- | --- | --- | --- | --- |
| Citric 1st pK | 4.65 | 3.13 | 1.49 | 52.3704 | 0.00068 | 0.03566 | 1− |
| Citric 2nd pK | 4.65 | 4.76 | 0.98 | 0.7915 | 0.01991 | 0.01576 | 2− |
| Citric 3rd pK | 4.65 | 6.39 | 0.73 | 0.0416 | 0.01513 | 0.00063 | 3− |
| Lauric Acid | 4.65 | 5.30 | 0.88 | 0.2703 | 0.10244 | 0.02768 | 1− |
| Imiquimod | 4.65 | 4.49 | 1.04 | 1.4193 | 0.05160 [Ammonium] | 0.07324 [Amine] | 1+ |

The calculated release from the data in Table 4 is 41.28%, and the actual measured release of Imiquimod from the composition reported in Table 3 after two hours is 39.36% by the technique described in Example 1.

Example 5

Figure 5:
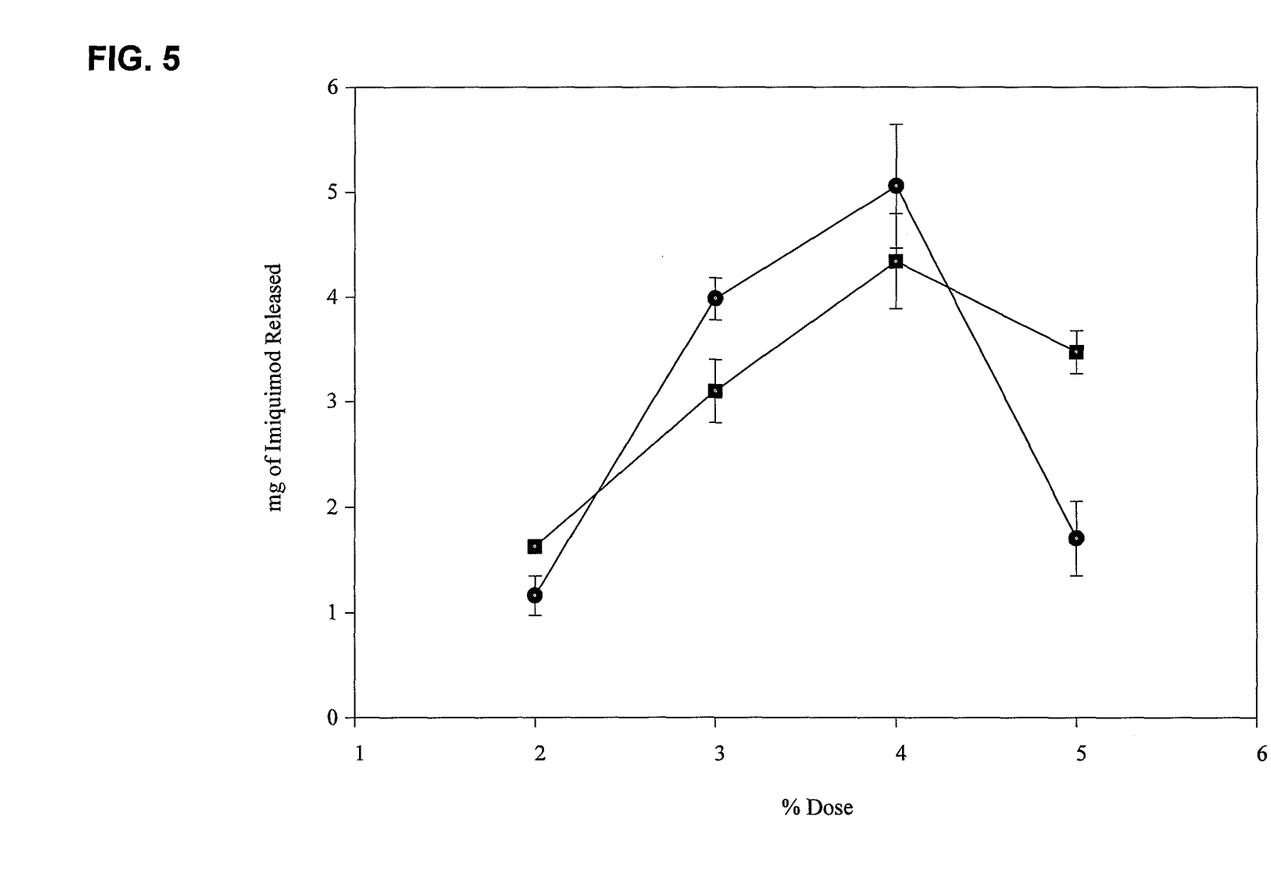
FIG. 5 is graph showing mean milligrams of Imiquimod released versus percent dose.

This example was carried out in order to determine how the release of Imiquimod was effected by the amount of Imiquimod in the formulation. The composition reported in Table 3 was modified to include 6.0 wt. % Imiquimod. In addition, sufficient Lauric acid was added to bind the Imiquimod to the polymer. The pH of a first series was 4.5 and the pH of a second series was 6.0. The expected result is that more Imiquimod will be released when more Imiquimod is present. The results are reported in FIG. 5. Unexpectedly, the highest release of Imiquimod was achieved at 4%, regardless of the pH.

The above specification, examples and data provide a complete description of the manufacture and use of the composition of the invention. Since many embodiments of the invention can be made without departing from the spirit and scope of the invention, the invention resides in the claims hereinafter appended.

We claim:
1. A cationic pharmaceutically active ingredient containing composition comprising:
(a) about 0.0001 wt. % to about 5 wt. % cationic pharmaceutically active ingredient comprising an aromatic amine or a salt of an aromatic amine;

(b) at least about 3 wt. % of a hydrophobic polymer/hydrophilic polymer adduct comprising a poly(vinylpyrrolidone-alkylene) polymer and a polymer comprising carboxylic acid groups, hydroxyl groups, or mixture of carboxylic acid groups and hydroxyl groups;

(c) at least 0.05 wt. % of a compatibilizing amount of a long chain organic acid having a carbon chain of about 10 to about 20 carbon atoms; and (d) at least about 50 wt. % water; and wherein the composition has a pH that is within about 2 pH units of the pK value of the cationic pharmaceutically active ingredient or within about 2 pH units of the pK value of the long chain organic acid.

2. A cationic pharmaceutically active ingredient containing composition according to claim 1, wherein the poly(vinylpyrrolidone-alkylene) polymer comprises a polymer having an alkylene group containing about 10 carbon atoms to about 30 carbon atoms.

3. A cationic pharmaceutically active ingredient containing composition according to claim 1, wherein the hydrophobic polymer/hydrophilic polymer adduct has a ratio of pyrrolidone groups to a combination of carboxylic acid groups and hydroxyl groups of about 1:1 to about 5:1.

4. A cationic pharmaceutically active ingredient containing composition according to claim 1, wherein the long chain organic acid has a carbon chain of about 12 carbon atoms to about 16 carbon atoms.

5. A cationic pharmaceutically active ingredient containing composition according to claim 1, wherein the long chain organic acid comprises at least one of lauric acid, stearic acid, palmitic acid, myristic acid, or a mixture thereof.

6. A cationic pharmaceutically active ingredient containing composition according to claim 1, wherein the composition comprises about 0.5 wt. % to about 6 wt. % of a surfactant.

7. A cationic pharmaceutically active ingredient containing composition according to claim 1, wherein the composition comprises about 0.1 wt. % to about 2 wt. % of a thickener.

8. A cationic pharmaceutically active ingredient containing composition according to claim 1, wherein the composition comprises about 0.5 wt. % to about 5 wt. % of a moisturizer.

9. A cationic pharmaceutically active ingredient containing composition according to claim 1, wherein the composition has a pH of about 3.5 to about 7.

10. A cationic pharmaceutically active ingredient containing composition according to claim 1, wherein a two hour release from a nylon membrane property of the cationic pharmaceutically active ingredient is less than 80%.

11. A cationic pharmaceutically active ingredient containing composition according to claim 1, wherein the cationic pharmaceutically active ingredient comprises an aromatic amine.

12. A cationic pharmaceutically active ingredient containing composition according to claim 1, wherein the cationic pharmaceutically active ingredient comprises a drug.

13. A cationic pharmaceutically active ingredient containing composition according to claim 1, wherein the cationic pharmaceutically active ingredient comprises Imiquimod.

14. A cationic pharmaceutically active ingredient containing composition according to claim 1, further comprising a pH adjusting agent.

15. A cationic pharmaceutically active ingredient containing composition according to claim 14, wherein the pH adjusting agent comprises sodium hydroxide, potassium hydroxide, triethanolamine, acetic acid, propionic acid, citric acid, succinic acid, or a mixture thereof.

16. A cationic pharmaceutically active ingredient containing composition according to claim 1, wherein the composition is provided as a topical composition for application to skin tissue.

17. A cationic pharmaceutically active ingredient containing composition according to claim 1, wherein the composition comprises at least 0.5 wt. % of the long chain organic acid.

18. A cationic pharmaceutically active ingredient containing composition according to claim 1, wherein the composition comprises about 0.5 wt. % to about 10 wt. % of the long chain organic acid.

19. A cationic pharmaceutically active ingredient containing composition according to claim 1, wherein the composition comprises about 1.0 wt. % to about 8 wt. % of the long chain organic acid.

* * * * *